US 011172949B2

(12) United States Patent
Baril et al.

(10) Patent No.: US 11,172,949 B2
(45) Date of Patent: Nov. 16, 2021

(54) TISSUE SPECIMEN RETRIEVAL DEVICES

(71) Applicant: COVIDIEN LP, Mansfield, MA (US)

(72) Inventors: Jacob C. Baril, Norwalk, CT (US); Amy L. Kung, Hamden, CT (US); Matthew A. Dinino, Newington, CT (US); Brian J. Creston, Madison, CT (US); Saumya Banerjee, Hamden, CT (US); Thomas A. Zammataro, North Haven, CT (US); Christopher M. Meehan, New Haven, CT (US); Scott J. Prior, Shelton, CT (US)

(73) Assignee: Covidien LP, Mansfield, MA (US)

( * ) Notice: Subject to any disclaimer, the term of this patent is extended or adjusted under 35 U.S.C. 154(b) by 122 days.

(21) Appl. No.: 16/595,422

(22) Filed: Oct. 7, 2019

(65) Prior Publication Data

US 2021/0100569 A1 Apr. 8, 2021

(51) Int. Cl.
*A61B 17/221* (2006.01)
*A61B 17/00* (2006.01)
*A61B 17/34* (2006.01)

(52) U.S. Cl.
CPC ........ *A61B 17/221* (2013.01); *A61B 17/3417* (2013.01); *A61B 2017/00287* (2013.01); *A61B 2017/00389* (2013.01); *A61B 2017/00991* (2013.01)

(58) Field of Classification Search
CPC .......... A61B 17/221; A61B 2017/2212; A61B 2017/00287
See application file for complete search history.

(56) References Cited

U.S. PATENT DOCUMENTS

| | | |
|---|---|---|
| 6,059,793 A | 5/2000 | Pagedas |
| 6,156,055 A | 12/2000 | Ravenscroft |
| 6,162,209 A | 12/2000 | Gobron et al. |
| 6,171,317 B1 | 1/2001 | Jackson et al. |
| 6,206,889 B1 | 3/2001 | Bennardo |
| 6,224,612 B1 | 5/2001 | Bates et al. |
| 6,228,095 B1 | 5/2001 | Dennis |
| 6,248,113 B1 | 6/2001 | Fina |
| 6,258,102 B1 | 7/2001 | Pagedas |
| 6,264,663 B1 | 7/2001 | Cano |
| 6,270,505 B1 | 8/2001 | Yoshida et al. |
| 6,280,451 B1 | 8/2001 | Bates et al. |
| 6,344,026 B1 | 2/2002 | Burbank et al. |
| 6,350,266 B1 | 2/2002 | White et al. |
| 6,350,267 B1 | 2/2002 | Stefanchik |

(Continued)

*Primary Examiner* — Wade Miles
(74) *Attorney, Agent, or Firm* — Carter, DeLuca & Farrell LLP (57) ABSTRACT

A tissue specimen retrieval device includes a first shaft and a second shaft telescopically movable relative to the first shaft. The second shaft supports an end effector assembly at a distal end thereof. The end effector assembly includes a tissue specimen bag supported by a first bag arm and a second bag arm. The first and second bag arms open the tissue specimen bag when the second shaft is in the deployed position. An insertion cap extends outwardly from the tissue specimen bag. The insertion cap retains the first and second bag arms at distal ends thereof. The insertion cap includes a release mechanism. The release mechanism releases the first and second bag arms from the insertion cap upon retraction of the second shaft from the deployed position.

20 Claims, 8 Drawing Sheets

(56) References Cited

U.S. PATENT DOCUMENTS

| | | |
|---|---|---|
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2016/0324515 A1* | 11/2016 | Ravikumar .......... A61B 17/221 |
| 2020/0337686 A1* | 10/2020 | Baril ................ A61B 17/00234 |

* cited by examiner

TISSUE SPECIMEN RETRIEVAL DEVICES

BACKGROUND

Technical Field

The present disclosure relates to tissue specimen retrieval from an internal body cavity and, more particularly, to tissue specimen retrieval devices to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

In accordance with an aspect of the present disclosure, a tissue specimen retrieval device includes a first shaft. A second shaft is telescopically movable relative to the first shaft. The second shaft supports an end effector assembly at a distal end thereof. The second shaft is movable relative to the first shaft between a retracted position in which the end effector assembly is disposed within the first shaft, and a deployed position in which the end effector assembly extends distally from the first shaft. The end effector assembly includes a tissue specimen bag supported by a first bag arm and a second bag arm. The first and second bag arms open the tissue specimen bag when the second shaft is in the deployed position. An insertion cap extends outwardly from the tissue specimen bag. The insertion cap retains the first and second bag arms at distal ends thereof. The insertion cap includes a release mechanism. The release mechanism releases the first and second bag arms from the insertion cap upon retraction of the second shaft from the deployed position.

In some aspects, the release mechanism includes first and second flanges. The flanges each include a distal end pivotably coupled to the insertion cap and a proximal end at a proximal portion of the insertion cap. The proximal ends of the flanges define an outer diameter at least equal to or greater than the outer diameter of the first shaft when the tissue specimen bag is moved to the deployed position. Each proximal end of each flange includes a locking arm extending inwardly toward the opposite locking arm. Each locking arm releasably retain the first and second bag arms such that upon retraction of the second shaft from the deployed position to the retracted position, the proximal ends of the flanges abut an outer periphery of the first shaft and cause the flanges to rotate outwardly relative to one another. This outward rotation causes the locking arms to release the first and second bag arms.

In some aspects, each bag arm includes a tang at a distal end thereof that includes an aperture defined therein. The apertures each receive at least one of the locking arms. The apertures of each bag arm overlap each other. A portion of each of the locking arms overlap each other.

In some aspects, the flanges are in a compressed position within the first shaft when the second shaft is in the retracted position and a first expanded position when the second shaft is in the deployed position. A distance between the proximal ends of the flanges in the first expanded position is equal to or greater than the outer diameter of the first shaft. A force of retraction of the second shaft from the deployed position to the retracted position brings the proximal ends of the flanges into abutment against the distal end of the first shaft to force the flanges into a second expanded position in which the locking arms are spaced apart from each other to release the first and second bag arms from the insertion cap.

In some aspects, an atraumatic tip is formed at a distal end of the insertion cap. The insertion cap includes a first body portion and a second body portion secured to the first body portion by at least one assembly pin. The first and second body portions form the atraumatic tip.

In some aspects, a suture loop is formed around a mouth of the tissue specimen bag. The suture loop cinches the mouth of the tissue specimen bag. The suture loop includes an extension loop extending from the insertion cap.

In accordance with an aspect of the present disclosure, a method of operating a tissue specimen retrieval device includes telescopically advancing a second shaft from a first shaft having. The second shaft supports an end effector assembly at a distal end thereof. Advancing the second shaft deploys the end effector assembly from the first shaft. The end effector assembly includes a tissue specimen bag supported by a first bag arm and a second bag arm. An insertion cap extends outwardly from the tissue specimen bag. The insertion cap retains the first and second bag arms. The insertion cap includes a release mechanism. The release mechanism releases the first and second bag arms from the insertion cap upon retraction of the second shaft from a deployed position. The second shaft is retracted into the first shaft to bring a proximal end of the insertion cap into abutment with a distal end of the first shaft. The first and second bag arms are released from the insertion cap by applying a force between the proximal end of the insertion cap and the distal end of the first shaft to actuate the release mechanism.

BRIEF DESCRIPTION OF THE DRAWINGS

The accompanying drawings, which are incorporated in and constitute a part of this specification, illustrate embodiments of the present disclosure and, together with the detailed description below, serve to further explain the present disclosure, in which.

DETAILED DESCRIPTION

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the present disclosure should typically be considered as available and applicable to other similar features or aspects in another exemplary embodiment of the present disclosure. Accordingly, technical features described herein according to one exemplary embodiment of the present disclosure may be applicable to other exemplary embodiments of the present disclosure, and thus duplicative descriptions may be omitted herein.

Exemplary embodiments of the present disclosure will be described more fully below (e.g., with reference to the accompanying drawings). Like reference numerals may refer to like elements throughout the specification and drawings.

Figure 1:
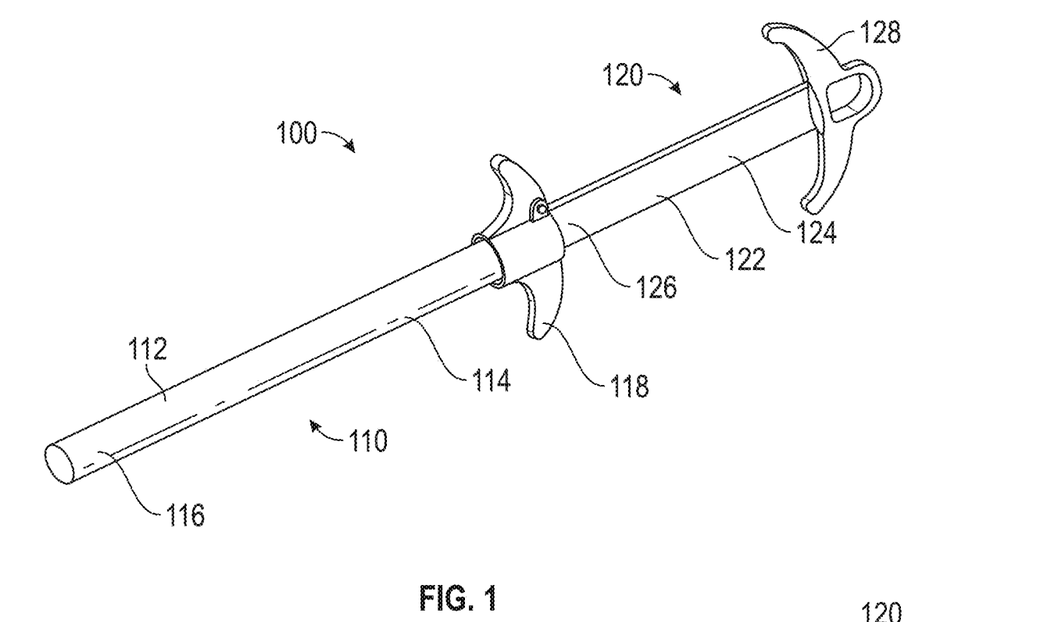
FIG. 1 is a perspective view of a tissue specimen retrieval device provided in accordance with aspects of the present disclosure, disposed in a retracted position.
Figure 2:
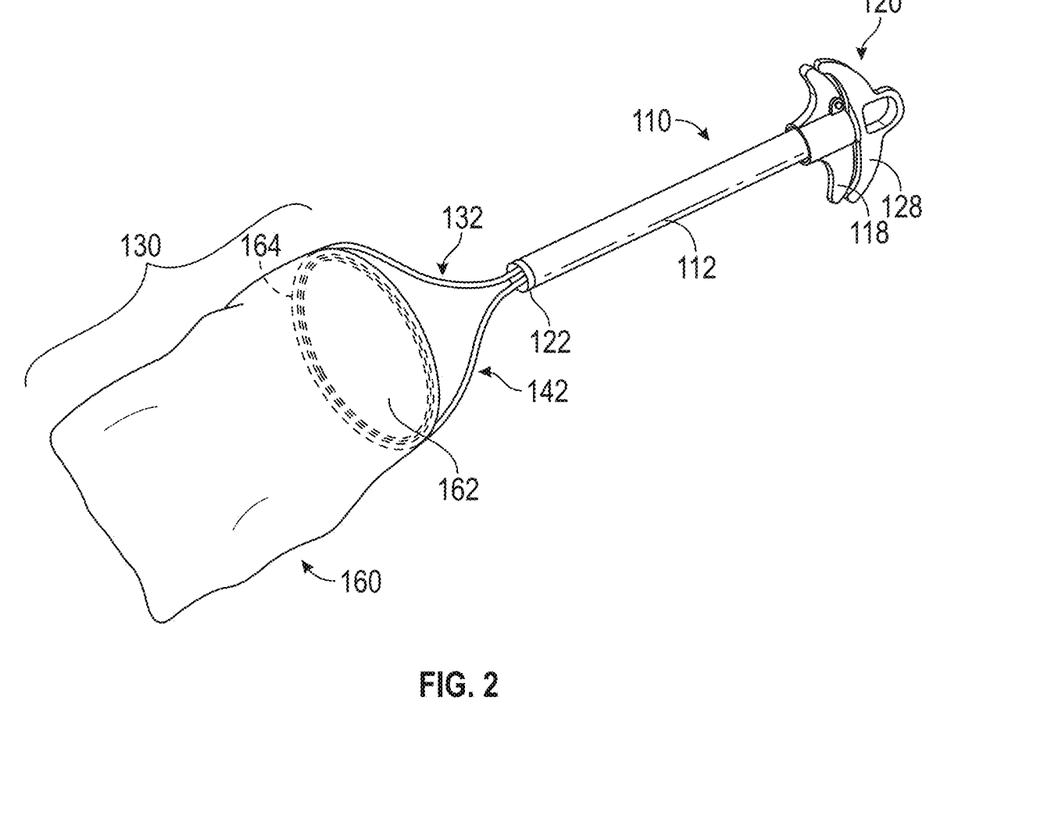
FIG. 2 is a perspective view of the tissue specimen retrieval device of FIG. 1, disposed in a deployed position.

Referring to FIGS. 1-2, a tissue specimen retrieval device provided in accordance with the present disclosure is shown generally identified by reference numeral 100. Tissue specimen retrieval device 100 includes a first body 110, a second body 120, and an end effector assembly 130 including a specimen bag 160. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112. The phrases "specimen bag" and "tissue specimen bag" may be used interchangeably herein.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2), wherein end effector assembly 130 extends distally from first shaft 112. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2) to move tissue specimen retrieval device 100 from the retracted position (FIG. 1), wherein end effector assembly 130 is disposed within first shaft 112, to the deployed position (FIG. 2), wherein end effector assembly 130 extends distally from first shaft 112.

Figure 3:
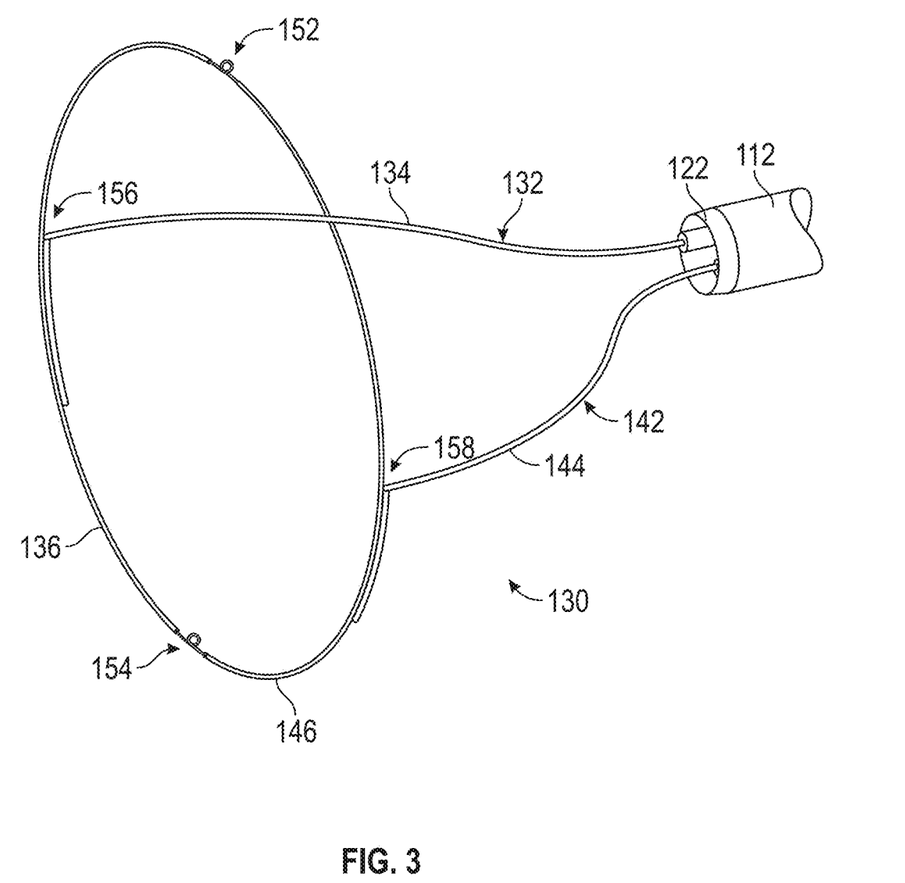
FIG. 3 is an enlarged, perspective view of the end effector assembly of the tissue specimen retrieval device of FIG. 1 with the specimen bag removed therefrom.

Referring to FIGS. 2 and 3, end effector assembly 130, as noted above, is supported at distal end portion 126 of second shaft 122. End effector assembly 130, more specifically, includes first and second arms 132, 142 extending distally from distal end portion 126 of second shaft 122 and a specimen bag 160 supported by and depending from first and second arms 132, 142. Each of first and second arms 132, 142 includes a proximal segment 134, 144 engaged with and extending distally from distal end portion 126 of second shaft 122, and a distal segment 136, 146 coupled to the respective proximal segment 134, 144 and extending distally therefrom. The phrases "arm" and "bag arm" may be used interchangeably herein.

Proximal segments 134, 144 of arms 132, 142, respectively, are substantially co-planar with one another so as to define a plane bisecting proximal segments 134 and 144, and are formed from resiliently flexible material, e.g., nitinol tubing, that biases proximal segments 134, 144 towards a first expanded position. Proximal segments 134, 144 each define, in the first expanded position, a curvature along at least a portion of the length thereof such that the proximal portions of proximal segments 134, 144 are relatively closer to one another and the distal portions of proximal segments 134, 144 are relatively father apart from one another.

Proximal segments 134, 144 of arms 132, 142, respectively, may be resiliently flexed from the first expanded position towards a first collapsed position, wherein the curvatures of proximal segments 134, 144 are at least partially eliminated and the distal portions of proximal segments 134, 144 are moved closer to one another, e.g., such that proximal segments 134, 144 are moved towards a substantially parallel orientation. Proximal segments 134, 144 are configured to resiliently flex within the plane defined thereby such that proximal segments 134, 144 remain substantially co-planar with one another in each of and during movement between the first expanded and first collapsed positions.

As an alternative or in addition to curved and/or resilient flexible configurations, proximal segments 134, 144 may define linear and/or substantially rigid configurations including one or more joints therealong to enable movement of proximal segments 134, 144 or portions thereof between the first expanded and first collapsed positions.

Distal segments 136, 146 of arms 132, 142, respectively, are substantially co-planar with one another so as to define a plane bisecting distal segments 136 and 146. Distal segments 136, 146 define curved configurations and are oriented relative to one another to cooperatively define a substantially oval-shaped configuration. Distal segments 136, 146 are formed from resiliently flexible material, e.g., nitinol tubing, that biases distal segments 136, 146 to a second expanded position, wherein distal segments 136, 146 cooperate to define a more-circular configuration.

Distal segments 136, 146 of arms 132, 142, respectively, are coupled to one another at first ends thereof via a first joint 152 and at second, opposite ends thereof via a second joint 154. In embodiments, first and second joints 152, 154 provide a bias that contributes to biasing distal segments 136, 146 towards the second expanded position; in other embodiments, the bias towards the second expanded position is provided by distal segments 136, 146 themselves without substantial bias imparted by first and second joints 152, 154. In either configuration, joints 152, 154 and distal segments 136, 146 are configured to move against the bias(es) such that distal segments 136, 146 are moved from the second expanded position, wherein distal segments 136, 146 cooperate to define the more-circular configuration, to a second collapsed position, wherein distal segments 136, 146 cooperate to define an elongated, oval-shaped configuration. Distal segments 136, 146 are configured to resiliently flex, and first and second joints 152, 154 are configured to move, within the plane defined by distal segments 136, 146, e.g., such that distal segments 136, 146 remain substantially co-planar with one another in each of and during movement between the second expanded and second collapsed positions. First and second joints 152, 154 may be hinge joints (living or multi-component hinges), pivot joints, torsion spring joints (similarly as detailed below), or other suitable joints.

As an alternative or in addition to distal segments 136, 146 cooperating to define an oval-shaped configuration and/or being resiliently flexible, distal segments 136, 146 may define linear and/or substantially rigid configurations including a plurality of joints, e.g., two to four joints, five joints, etc., defining a polygonal configuration, while still being movable between the second expanded position and the second collapsed position.

With reference to FIG. 2, distal segments 136, 146 support specimen bag 160 thereon with specimen bag 160 depending therefrom. Specimen bag 160 may be formed from any suitable bio-compatible material (or materials), e.g., ripstop nylon, configured to retain a tissue specimen therein. Specimen bag 160 defines at least one opening, e.g., open end 162 thereof, for receipt of a tissue specimen therein. Specimen bag 160 may include one or more channels 164 formed about at least a portion of the perimeter of open end 162 thereof for retaining distal segments 136, 146 of arms 132, 142, respectively, therein to support specimen bag 160 on distal segments 136, 146. Alternatively, open end 162 of specimen bag 160 may be welded, adhered, or otherwise affixed to or about distal segments 136, 146 to support specimen bag 160 thereon.

The one or more openings of specimen bag 160, e.g., open end 162, may include a cinch cord (not shown) disposed thereabout to enable selective closure of the opening. Specimen bag 160 may be disengaged from distal segments 136, 146 upon cinching closed open end 162 of specimen bag 160, retraction of end effector assembly 130 back towards the retracted position (FIG. 1), using a separate instrument, e.g., grasping device, and/or in any other suitable manner Turning again to FIGS. 2 and 3, distal segments 136, 146 of arms 132, 142 are coupled to respective proximal segments 134, 144 of arms 132, 142 via third and fourth joints 156, 158, respectively, to enable the collapsing of end effector assembly 130 wherein distal segments 136, 146 are collapsed onto to proximal segments 134, 144. Third and fourth joints 156, 158 may be hinge joints (living or multi-component hinges), pivot joints, torsion spring joints (similarly as detailed below), or other suitable joints. Third and fourth joints 156, 158, more specifically, enable collapsing of distal segments 136, 146 relative to proximal segments 134, 144 from a third expanded position (see FIG. 4A), wherein the planes defined by distal segments 136, 146 and proximal segments 134, 144 are disposed in a first orientation relative to one another, to a third collapsed position (see FIG. 4B), wherein the planes defined by distal segments are disposed in a second orientation relative to one another. Third and fourth joints 156, 158 are configured to bias distal segments 136, 146 towards the third expanded position relative to proximal segments 134, 144, wherein the planes defined thereby are disposed in the first orientation, although other configurations are also contemplated.

Figure 4A:
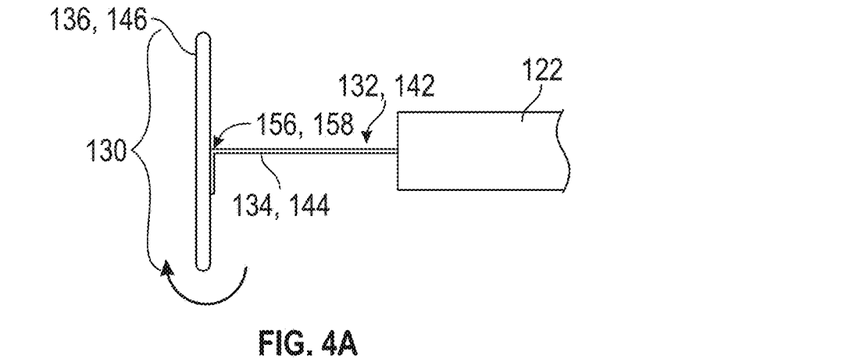
FIGS. 4A and 4B are side views of the end effector assembly of the tissue specimen retrieval device of FIG. 1 illustrating a first collapsing of the end effector assembly.

In embodiments, in the third expanded position, corresponding to the first orientation of the planes defined by distal segments 136, 146 and proximal segments 134, 144, the planes are disposed in substantially perpendicular orientation relative to one another; in other embodiments, the planes define an angle therebetween of approximately 45 degrees to approximately 120 degrees; in still other embodiments, the planes define an angle therebetween of approximately 60 degrees to approximately 105 degrees; and in yet other embodiments, the planes define an angle therebetween of approximately 75 degrees to approximately 90 degrees.

Figure 4B:
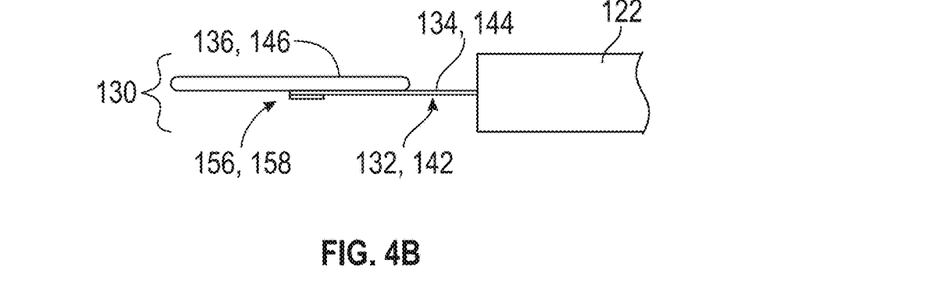

In embodiments, in the third collapsed position, corresponding to the second orientation of the planes defined by distal segments 136, 146 and proximal segments 134, 144, the planes are disposed in substantially parallel orientation relative to one another; in other embodiments, the planes define an angle therebetween of approximately 0 degrees to approximately 15 degrees; in still other embodiments, the planes define an angle therebetween of approximately 0 degrees to approximately 10 degrees; and in yet other embodiments, the planes define an angle therebetween of approximately 0 degrees to approximately 5 degrees.

Turning back to FIGS. 1 and 2, in the retracted position of tissue specimen retrieval device 100 (FIG. 1), as noted above, end effector assembly 130 is disposed within first shaft 112 of first body 110. In order to fit end effector assembly 130 within first shaft 112 in the retracted position of tissue specimen retrieval device 100 (FIG. 1), the end effector assembly 130 is collapsed from two orientations. Although described herein in terms of a first collapse followed by a second collapse, the present disclosure also contemplates that the first collapse follows the second collapses, or that at least portions of the first and second collapses are effected substantially simultaneously.

Referring to FIGS. 4A and 4B, the first collapse corresponds to the movement of distal segments 136, 146 of arms 132, 142 about third and fourth joints 156, 158, respectively, and relative to respective proximal segments 134, 144 from the third expanded position to the third collapsed position, as detailed above. This movement of distal segments 136, 146 about third and fourth joints 156, 158 to effect the first collapse occurs via relative movement of the planes defined by proximal segments 134, 144 and distal segments 136, 146, e.g., the plane defined by distal segments 136, 146 is moved relative to the plane defined by proximal segments 134, 144 during the first collapse.

Figure 5A:
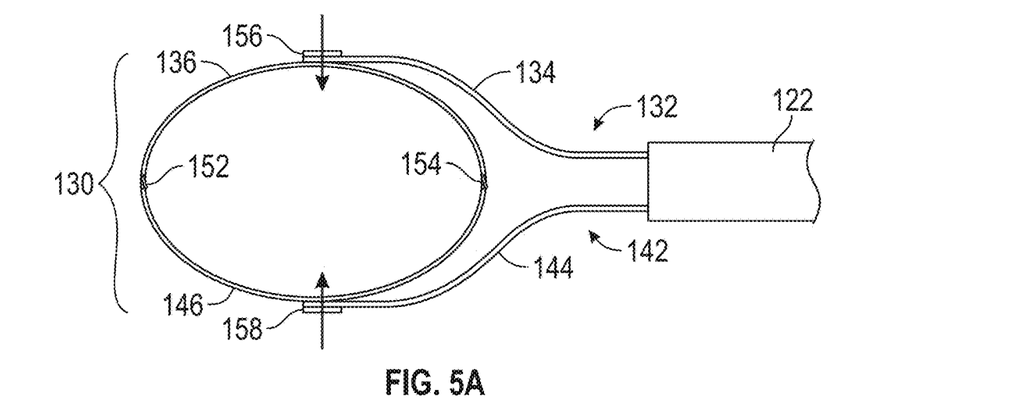
FIGS. 5A and 5B are top views of the end effector assembly of the tissue specimen retrieval device of FIG. 1 illustrating a second collapsing of the end effector assembly.
Figure 5B:
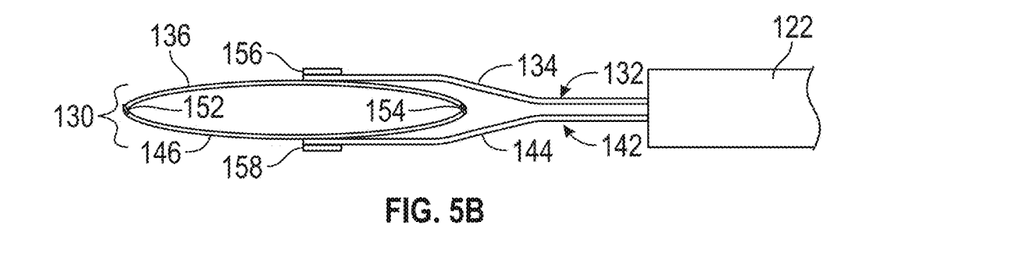

The second collapse, illustrated in FIGS. 5A and 5B, is a compound collapse corresponding to the flexion and movement about joints 152, 152 of distal segments 136, 146 of arms 132, 142, respectively, from the second expanded position to the second collapsed position, as detailed above, as well as flexion of proximal segments 134, 144 of arms 132, 142 from the first expanded position to the first collapsed position, as also detailed above. These movements corresponding to the second collapse occur within the planes defined by proximal segments 134, 144 and distal segments 136, 146, respectively such that the planes defined by proximal segments 134, 144 and distal segments 136, 146 remain substantially stationary relative to one another during the second collapse.

With additional reference to FIGS. 1 and 2, once the first and second collapses are effected, as detailed above, specimen bag 160 may be folded, twisted, wrapped, rolled, and/or otherwise manipulated relative to arms 132, 142 and, thereafter, second shaft 122 may be pulled proximally relative to first shaft 112, e.g., via moving second handle 128 away from first handle 118, thereby drawing end effector 130 into first shaft 112 to the retracted position. As an alternative to initially manipulating specimen bag 160 relative to arms 132, 142 before drawing end effector 130 into first shaft 112, arms 132, 142 of end effector assembly 130 may instead be at least partially drawn into first shaft 112 followed by manipulating specimen bag 160 to fit within first shaft 112. In other embodiments, rather than effecting the first and second collapses in the deployed position and the retracting end effector assembly 130 proximally into first shaft 112, end effector assembly 130, after the first and second collapses are effected, may be inserted through the proximal end portion 114 of first shaft 112 and moved therethrough to the retracted position, e.g., via manipulating second handle 128. Other suitable configurations for loading end effector assembly 130 within first shaft 112 are also contemplated. Regardless of the loading configuration, once loaded within first shaft 112 in the retracted position, the first and second collapses of arms 132, 142 of end effector assembly 130 are maintained against the biases thereof via the internal spatial constraints of first shaft 112.

Continuing with reference to FIGS. 1 and 2, with end effector assembly 130 loaded within first shaft 112 and tissue specimen retrieval device 100 disposed in the retracted position (FIG. 1), tissue specimen retrieval device 100 is ready for use. More specifically, tissue specimen retrieval device 100 may be inserted into an internal surgical site, e.g., through a suitable access device (not shown), and thereafter moved from the retracted position to the deployed position, e.g., via grasping second handle 128 and moving second handle 128 towards first handle 118.

As end effector assembly 130 is deployed from first shaft 112 and, thus, is no longer constrained by first shaft 112, proximal segments 134, 144 of arms 132, 142 are returned from the first collapsed position to the first expanded position, distal segments 136, 146 of arms 132, 142 are returned from the second collapsed position back to the second expanded position, and distal segments 136, 146 are returned relative to proximal segments 134, 144 from the third collapsed position to the third expanded position. The return to the first, second, and third expanded positions may occur in any order and/or portions thereof may occur substantially simultaneously. Further, upon return to the first, second, and/or third expanded positions, specimen bag 160 is unfurled and open end 162 thereof presented to facilitate insertion of a tissue specimen therein during use. Unless specified to the contrary below, the tissue specimen retrieval device described in more detail below with reference to FIGS. 6A, 6B, 7A, 7B, 8, 9A, 9B, 10A, 10B and 10C is substantially the same as the specimen retrieval device 100 described above. Thus, wherever technically feasible, the features described with respect to the specimen retrieval device 100 are similarly available to the tissue specimen retrieval device described in more detail below with reference to FIGS. 6A to 10C.

Figure 6A:
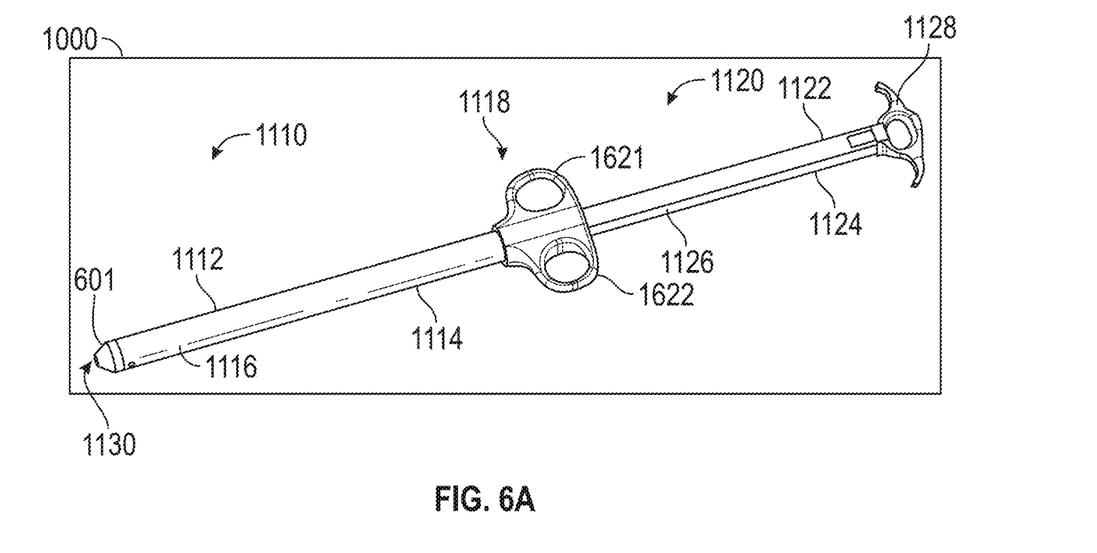
FIG. 6A is a perspective view of a tissue specimen retrieval device including an insertion cap disposed in a retracted position in accordance with aspects of the present disclosure.
Figure 6B:
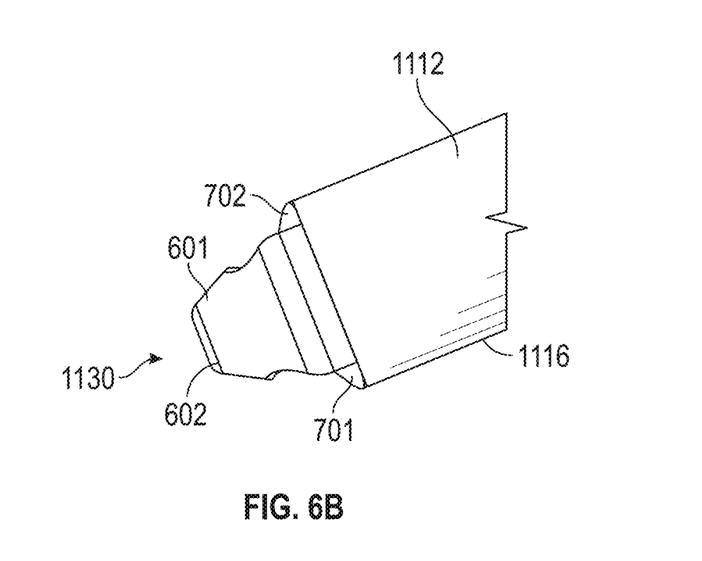
FIG. 6B is an enlarged perspective view of a distal end of a tissue specimen retrieval device of FIG. 6A including an insertion cap disposed in a retracted position in accordance with aspects of the present disclosure.
Figure 7A:
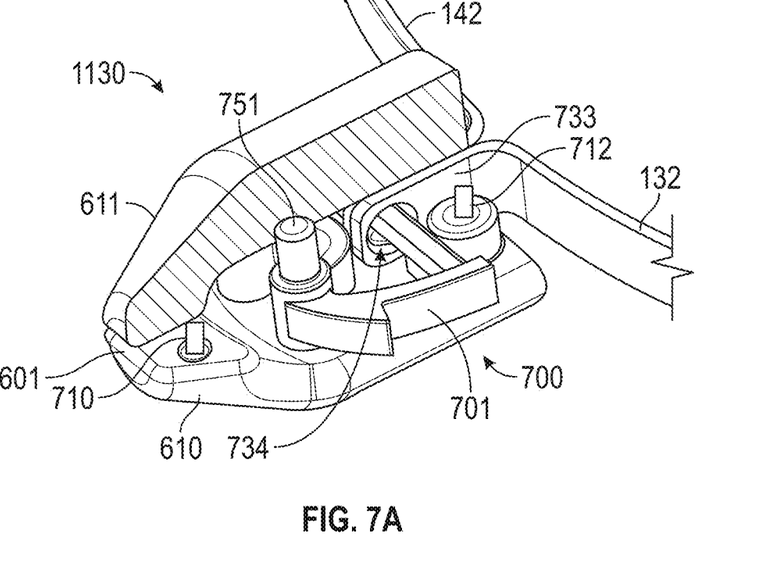
FIG. 7A is an enlarged, interior perspective view of the insertion cap of FIG. 6B showing a release mechanism secured to first and second arms of the tissue specimen retrieval device.
Figure 7B:
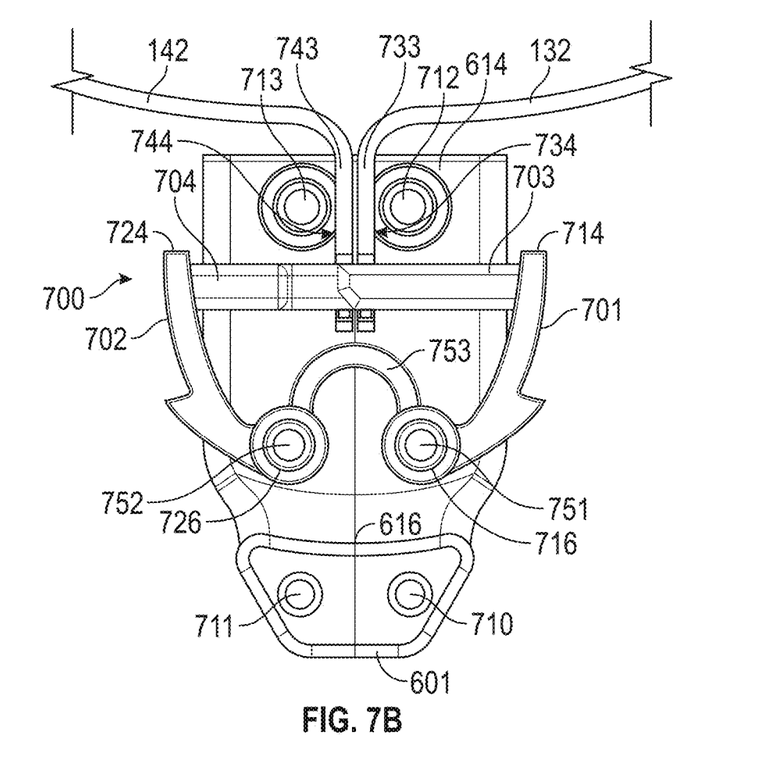
FIG. 7B is an internal plan view of the release mechanism of FIG. 7A.
Figure 8:
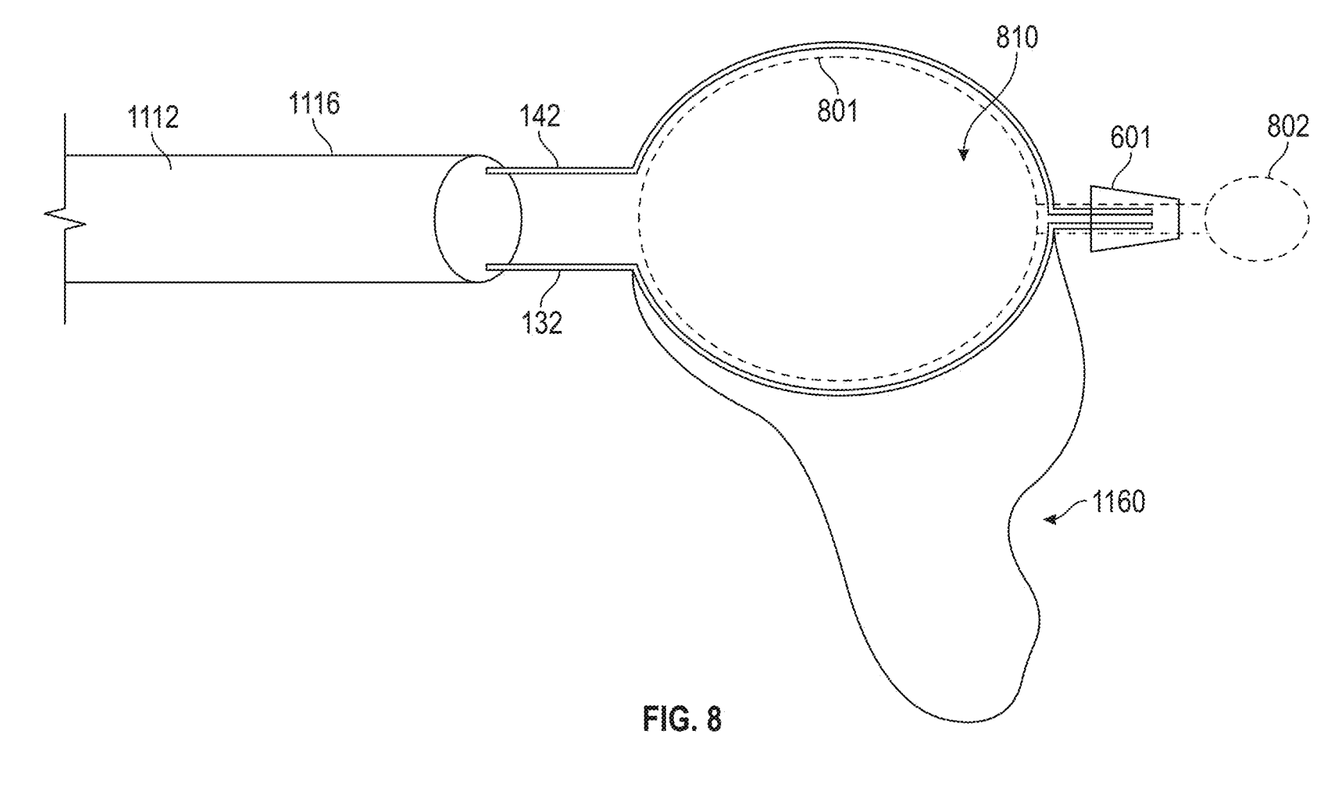
FIG. 8 is a schematic plan view of a suture loop around a mouth of a tissue specimen bag and an extension loop extending from an insertion cap in accordance with aspects of the present disclosure.

Referring to FIGS. 6A, 6B and 8, a similar tissue specimen retrieval device 1000 is shown that includes a first body 1110 and a second body 1120. The tissue specimen retrieval device 1000 includes a first shaft 1112 and a second shaft 1122 telescopically movable relative to the first shaft 1112. The second shaft 1122 supports an end effector assembly 1130 at a distal end portion 1116 thereof. The second shaft 1122 is movable relative to the first shaft 1112 between a retracted position (see, e.g., FIGS. 6A and 6B), in which the end effector assembly 1130 is disposed within the first shaft 1112, and a deployed position (see, e.g., FIG. 8), in which the end effector assembly 1130 extends distally from the first shaft 1112. Movement of the second shaft 1122 from the retracted position to the deployed position advances the end effector assembly 1130 out of the first shaft 1112 and deploys the end effector assembly 1130 including a tissue specimen bag (see, e.g., FIG. 2), which is described in more detail below. Thus, the tissue specimen bag 1160 (see, e.g., FIG. 8) is positioned along an interior space of the first shaft 1112 when the second shaft 1122 is in the retracted position. The tissue specimen bag 1160 is in a furled configuration while positioned in the first shaft 1112 and unfurls when deployed from the first shaft 1112.

In embodiments, a first handle 1118 is disposed at a proximal portion 1114 of the first shaft 1112 and a second handle 1128 is disposed at a proximal potion 1124 of the second handle 1128. The first and second handles 1118 and 1128 are relatively movable to move the second shaft 1122 between the retracted and deployed positions. The first handle 1118 includes first and second finger loops 1621 and 1622. The finger loops 1621 and 1622 allow a user to hold the first shaft 1112 in position while the second shaft 1122 is telescopically advanced to move the second shaft 1122 between the retracted and deployed positions.

Referring to FIGS. 6A to 10C, the end effector assembly 1000 includes a tissue specimen bag 1160 supported by a first bag arm 132 and a second bag arm 142. The first and second bag arms 132 and 142 open the tissue specimen bag when the second shaft 1122 is in the deployed position. An insertion cap 601 extends outwardly from the tissue specimen bag 1160. The insertion cap 601 retains the first and second bag arms 132 and 142 at distal ends thereof (see, e.g., tangs 733 and 743 described in more detail below). The insertion cap 601 includes a release mechanism 700. The release mechanism 700 releases the first and second bag arms 732 and 742 from the insertion cap 601 upon retraction of the second shaft 1122 from the deployed position. The bag arms 132 and 142 can then be separated from the tissue specimen bag 1160 and retracted through the first shaft 1112 (see, e.g., FIG. 9B).

In embodiments, the release mechanism 700 includes first and second flanges 701 and 702. The first flange 701 has a distal end 716 and the second flange 702 has a distal end 726 each pivotably coupled to the insertion cap 601 about a pivot pin. The first flange 701 rotates about pivot pin 751 and the second flange 702 rotate about pivot pin 752. In an exemplary embodiment, pivot pins 751 and 752 each include a torsion spring configured to bias the first and second flanges 701 and 702 into a first expanded configuration (see, e.g., FIG. 10B) having a first diameter. In an exemplary embodiment, Flanges 701 and 702 include a common hinge disposed therebetween, e.g., a living hinge 703, that biases the flanges 701 and 701 outwardly relieve to one another (e.g., into the first expanded configuration described with reference to FIG. 10B) to open to the first diameter. The interior periphery of shaft 1112 maintains the flanges 701, 702 in a compressed orientation (e.g. less than the first diameter—see, e.g., FIG. 10A) to bias the flanges 701, 702 inwardly when the cap 601 is seated within shaft 1112 and prior to deployment of the tissue specimen bag 1160 (see, e.g., FIG. 6B). Upon deployment of the tissue specimen bag 1160 from the first shaft 1112, the flanges 702 and 701 deflect outwardly to the first diameter therebetween (see, e.g., FIG. 10B) relative to one another under the bias of hinge 703.

The first flange 701 has a proximal end 714 and the second flange 702 has a proximal end 724 each disposed at a proximal portion 614 of the insertion cap 601. The proximal ends 714 and 724 of the flanges 701 and 702 define an outer diameter therebetween (see, e.g., line X-X in FIG. 9A) at least equal to or greater than the outer diameter (see, e.g., line Y-Y in FIG. 9A) of the first shaft 1112 after the second shaft 1122 is moved to the deployed position.

Each proximal end 714 and 724 of each flange 701 and 702 includes a locking arm (703 and 704, respectively) extending inwardly toward the opposite locking arm. Each locking arm 703, 704 is configured to releasably retain the distal ends or tangs 733, 743 of each respective arm 132, 142. More particularly, prior to release of the arms 132, 142, the locking arms 703, 704 are overlapped relative to one another and align to receive the tangs 733, 743 of each arm 132, 142 (see, e.g., FIGS. 10A-10C).

Figure 9A:
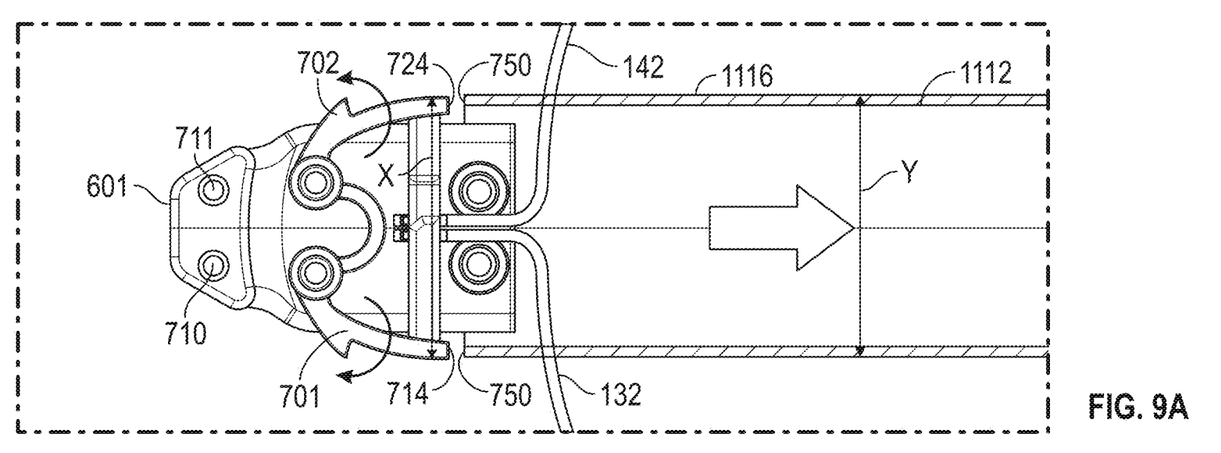
FIG. 9A is an internal plan view of the release mechanism of FIG. 7A as the insertion cap is retracted toward the first shaft of the tissue specimen retrieval device.
Figure 9B:
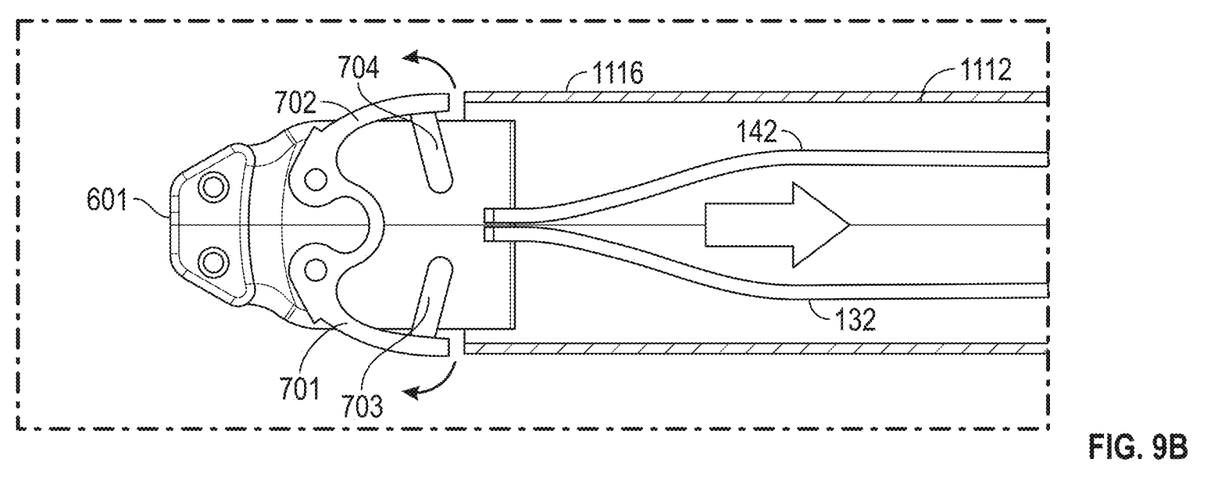
FIG. 9B is an internal plan view of the release mechanism of FIG. 9A illustrating a process of releasing the first and second arms of the tissue specimen retrieval device from the insertion cap.

Upon retraction of the second shaft 1122 from the deployed position to the retracted position, the proximal ends 714 and 724 of the flanges 701 and 702 abut an outer periphery 750 of the first shaft 112 and cause the flanges 701 and 702 to rotate further outwardly relative to one another from the first diameter (see, e.g., FIGS. 9A to 9B). This outward rotation causes the locking arms 703 and 704 to release the first and second bag arms 132 and 142.

Figure 10A:
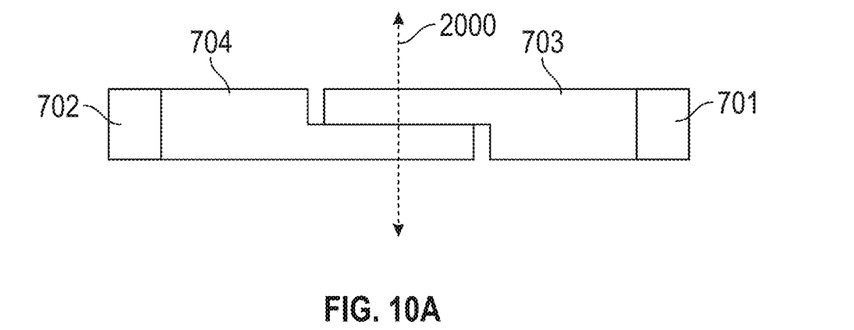
FIG. 10A is a schematic cross-sectional view of the first and second release arms of the release mechanism of FIG. 9A along the line X-X before the insertion cap is deployed from the first shaft of the tissue specimen retrieval device.
Figure 10B:
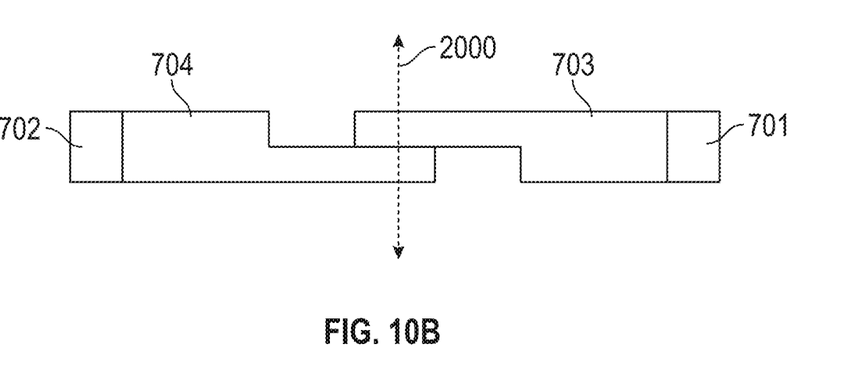
FIG. 10B is a schematic cross-sectional view of the first and second release arms of the release mechanism of FIG. 9A along the line X-X after the insertion cap is deployed from the first shaft of the tissue specimen retrieval device.
Figure 10C:
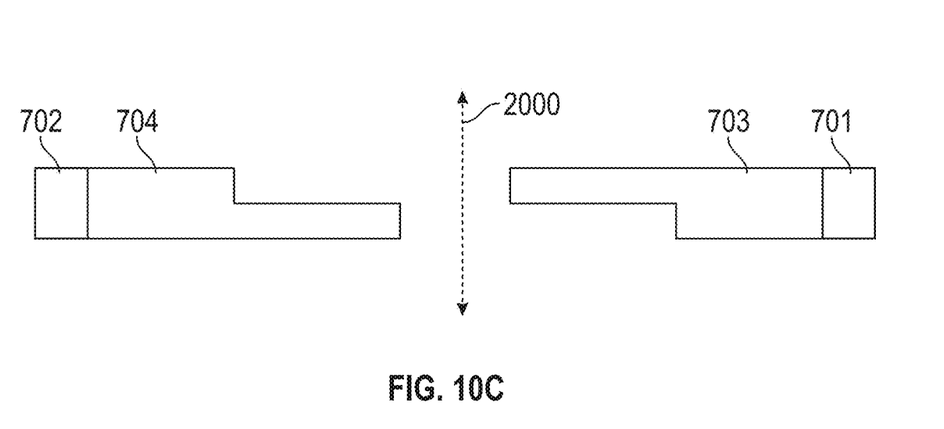
FIG. 10C is a schematic cross-sectional view of the first and second release arms of the release mechanism of FIG. 9A along the line X-X when the first and second arms of the tissue specimen retrieval device are released from the insertion cap.

In embodiments, each bag arm 132 and 142 includes a tang (733 and 743, respectively) at a distal end thereof that includes an aperture (734 and 744, respectively) defined therein. The apertures 734 and 744 each receive one of the locking arms 703 and/or 704. The apertures 734 and 744 of each bag arm 132 and 142 overlap each other. Thus, the apertures 734 and 744 may be substantially aligned with each other.

In embodiments, the flanges 701 and 702 are in a compressed position within the first shaft 1112 (see, e.g., FIGS. 6B and 10A) when the second shaft 1122 is in the retracted position and move to a first expanded position (see, e.g., FIGS. 9A and 10B) when the second shaft 122 is deployed. A distance between the proximal ends 714 and 724 of the flanges 701 and 702 in the first expanded position (as mentioned above, the first diameter) is equal to or slightly greater than the outer diameter of the first shaft (see, e.g., FIG. 9A).

The force of retraction of the second shaft 1122 from the deployed position to the retracted position brings the proximal ends 714 and 724 of the flanges 701 and 702 into abutment against the distal end 1116 of the first shaft 1112 and forces the flanges 701 and 702 outwardly relative to one another into a second expanded position (see, e.g., FIGS. 9B and 10C) which, in turn, forces the locking arms 703 and 704 to release the first and second bag arms 132 and 142 from the insertion cap 601.

FIGS. 10A to 10C illustrate a reference line 2000 which is used to show relative spacing between the first and second locking arms 703 and 704 when the flanges 701 and 702 are in the compressed position (FIG. 10A), the first expanded position (FIG. 10B) and the second expanded position (FIG. 10C).

In embodiments, an atraumatic tip or tapered tip 602 (See FIG. 6B) is formed at a distal end of the insertion cap 601. The insertion cap 601 includes a first body portion 610 and a second body portion 611 secured to the first body portion 610 by one or more assembly pins (e.g., assembly pins 710 and 711 at distal end portion 616 of the insertion cap 601, and assembly pins 712 and 713 at proximal end portion 614 of the insertion cap 601). The assembly pins 710, 711, 712 and 713 are configured to protrude from the first and/or second body portion 610 and 611 may be secured in (e.g., may be fixedly attached to) corresponding indents formed on the opposite body portion. The first and second body portions 610 and 611 may combine form the atraumatic tip 602.

In embodiments, the insertion cap 601 (e.g., including the atraumatic insertion tip 602) includes or is formed of plastic or silicon. However, exemplary embodiments of the present disclosure are not limited thereto and other materials may be employed to form the insertion cap 601; particularly for forming the atraumatic insertion tip 602 of the insertion cap 601.

In embodiments, a suture loop 801 is formed around a mouth 810 of the tissue specimen bag (see, e.g., FIG. 8). The suture loop 801 can be used to cinch the mouth 810 of the tissue specimen bag 160, 1160. The tissue specimen bag 160, 1160 may be cinched closed after the first and second bag arms 132 and 142 have been separated from the insertion cap 601 and are retracted through the first shaft 1112. The suture loop 801 may include an extension loop 802 extending from the insertion cap 601. The extension loop 802 may also be used to cinch the bag mouth 810 closed.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
a first shaft including an outer diameter;
a second shaft telescopically movable relative to the first shaft, the second shaft supporting an end effector assembly at a distal end thereof and movable relative to the first shaft between a retracted position, wherein the end effector assembly is disposed within the first shaft, and a deployed position, wherein the end effector assembly extends distally from the first shaft,
the end effector assembly including a tissue specimen bag supported by a first bag arm and a second bag arm, the first and second bag arms configured to open the tissue specimen bag when the second shaft is in the deployed position; and
an insertion cap disposed on and extending outwardly from the tissue specimen bag, the insertion cap configured to retain the first and second bag arms at distal ends thereof, the insertion cap including a release mechanism configured to release the first and second bag arms from the insertion cap upon retraction of the second shaft from the deployed position.

2. The tissue specimen retrieval device according to claim 1, wherein the release mechanism includes:
first and second flanges each including a distal end pivotably coupled to the insertion cap and a proximal end disposed at a proximal portion of the insertion cap, the proximal ends of the flanges defining an outer diameter therebetween at least equal to or greater than the outer diameter of the first shaft when the tissue specimen bag is moved to the deployed position, each proximal end of each flange including a locking arm extending inwardly toward the opposite locking arm, each locking arm configured to releasably retain the first and second bag arms such that upon retraction of the second shaft from the deployed position to the retracted position, the proximal ends of the flanges abut an outer periphery of the first shaft and cause the flanges to rotate outwardly relative to one another, which, in turn, causes the locking arms to release the first and second bag arms.

3. The tissue specimen retrieval device according to claim 2, wherein each bag arm includes a tang at a distal end thereof that includes an aperture defined therein configured to operably receive at least one of the locking arms.

4. The tissue specimen retrieval device according to claim 3, wherein the apertures of each bag arm overlap each other.

5. The tissue specimen retrieval device according to claim 2, wherein the flanges are disposed in a compressed position within the first shaft when the second shaft is in the retracted position and a first expanded position when the second shaft is in the deployed position.

6. The tissue specimen retrieval device according to claim 5, wherein the flanges each include a spring configured to bias the flanges into the first expanded position.

7. The tissue specimen retrieval device according to claim 5, wherein the flanges are connected with each other by a hinge configured to bias the flanges into the first expanded position.

8. The tissue specimen retrieval device according to claim 5, wherein a distance between the proximal ends of the flanges in the first expanded position is equal to or greater than the outer diameter of the first shaft.

9. The tissue specimen retrieval device according to claim 8, wherein a force of retraction of the second shaft from the deployed position to the retracted position brings the proximal ends of the flanges into abutment against the distal end of the first shaft to force the flanges into a second expanded position in which the locking arms are spaced apart from each other to release the first and second bag arms from the insertion cap.

10. The tissue specimen retrieval device according to claim 1, further comprising an atraumatic tip formed at a distal end of the insertion cap.

11. The tissue specimen retrieval device of claim 10, wherein the insertion cap includes a first body portion and a second body portion secured to the first body portion by a plurality of assembly pins, the first and second body portions forming the atraumatic tip.

12. The tissue specimen retrieval device of claim 1, further comprising a suture loop formed around a mouth of the tissue specimen bag, the suture loop configured to cinch the mouth of the tissue specimen bag.

13. The tissue specimen retrieval device of claim 12, wherein the suture loop includes an extension loop extending from the insertion cap.

14. A tissue specimen retrieval device, comprising:
a first shaft including an outer diameter;
a second shaft telescopically movable relative to the first shaft, the second shaft supporting an end effector assembly at a distal end thereof and movable relative to the first shaft between a retracted position, wherein the end effector assembly is disposed within the first shaft, and a deployed position, wherein the end effector assembly extends distally from the first shaft,
the end effector assembly including a tissue specimen bag supported by a first bag arm and a second bag arm, the first bag arm including a first tang defining a first aperture and the second bag arm including a second tang defining a second aperture, the first and second bag arms configured to open the tissue specimen bag when the second shaft is in the deployed position; and
an insertion cap disposed on and extending from the tissue specimen bag, the insertion cap configured to retain the first and second bag arms at distal ends thereof, the insertion cap including a first locking arm removably positioned in the first aperture of the first bag arm and a second locking arm removably position in the second aperture of the second bag arm, the insertion cap including a release mechanism configured to release the first and second bag arms from the insertion cap upon retraction of the second shaft from the deployed position by removing the first locking arm from the first aperture and the second locking arm from the second aperture and retracting the first bag arm and the second bag arm.

15. The tissue specimen retrieval device according to claim 14, further including a first flange pivotably coupled to the insertion cap and supporting the first locking arm and a second flange pivotably coupled to the insertion cap and supporting the second locking arm.

16. The tissue specimen retrieval device according to claim 15, wherein the flanges are disposed in a compressed position within the first shaft when the second shaft is in the retracted position and a first expanded position when the second shaft is in the deployed position.

17. The tissue specimen retrieval device according to claim 16, wherein the flanges each include a spring configured to bias the flanges into the first expanded position.

18. The tissue specimen retrieval device according to claim 16, wherein the flanges are connected with each other by a hinge configured to bias the flanges into the first expanded position.

19. The tissue specimen retrieval device according to claim 16, wherein a distance between proximal ends of the flanges in the first expanded position is equal to or greater than the outer diameter of the first shaft.

20. The tissue specimen retrieval device according to claim 19, wherein a force of retraction of the second shaft from the deployed position to the retracted position brings the proximal ends of the flanges into abutment against the distal end of the first shaft to force the flanges into a second expanded position in which the locking arms are spaced apart from each other to release the first and second bag arms from the insertion cap.

* * * * *